United States Patent [19]

Punja et al.

[11] 4,298,616
[45] Nov. 3, 1981

[54] FUNGICIDAL ACYLANILIDE COMPOUNDS

[75] Inventors: Nazim Punja, Crowthorne; William G. Rathmell, Wokingham, both of England

[73] Assignee: Imperial Chemical Industries Limited, London, England

[21] Appl. No.: 197,681

[22] Filed: Oct. 16, 1980

[30] Foreign Application Priority Data

Nov. 2, 1979 [GB] United Kingdom ............... 37968/79

[51] Int. Cl.³ .................. A01N 43/08; C07D 307/68; C07D 307/73
[52] U.S. Cl. .................................. 424/285; 260/347.3
[58] Field of Search ...................... 260/347.3; 424/285

[56] References Cited

U.S. PATENT DOCUMENTS

| 2,384,811 | 9/1945 | Coleman et al. | 260/562 |
| 3,048,619 | 8/1962 | Pray | 260/471 |
| 3,249,625 | 5/1966 | Bestian et al. | 260/326.5 |
| 3,268,583 | 8/1966 | Moore et al. | 260/561 |
| 3,274,170 | 9/1966 | Levenkusen et al. | 260/112.5 |
| 4,013,684 | 3/1977 | Merkle et al. | 260/347.3 |
| 4,021,224 | 5/1977 | Pallos et al. | 71/88 |

OTHER PUBLICATIONS

Melikyan et al., Chemical Abstracts, vol. 89, (1978), 75,356s.

Primary Examiner—Richard Raymond
Attorney, Agent, or Firm—Cushman, Darby & Cushman

[57] ABSTRACT

This invention relates to alkynyl acylanilide derivatives useful as pesticides, to a process for preparing them, to pesticidal compositions containing them, and to a method of combating pests using them.

6 Claims, No Drawings

FUNGICIDAL ACYLANILIDE COMPOUNDS

The invention provides alkynyl acylanilide derivatives having the formula:

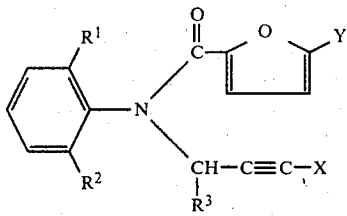

wherein $R^1$ and $R^2$ are lower alkyl groups containing from 1 to 4 carbon atoms; $R^3$ is hydrogen or a lower alkyl group containing from 1 to 4 carbon atoms; X is hydrogen or halogen; and Y is halogen, nitro or an alkoxy group containing from 1 to 4 carbon atoms.

Preferred compounds are those wherein $R^1$, $R^2$ and $R^3$ are methyl radicals, X is hydrogen, bromine, iodine or chlorine, and Y is chlorine, bromine, nitro or methoxy.

The invention further provides a process for combating pests, especially fungi, which comprises applying to plants or seeds, or to their loci, an acylanilide derivative as defined above and hereinbelow.

The invention also provides pesticidal compositions especially anti-fungal compositions comprising as an active ingredient an alkynyl acylanilide derivative as defined in any of the preceding paragraphs, and in the paragraph and Tables below.

In a particularly preferred aspect the invention provides, as novel chemical compounds, the derivatives having the formulae:

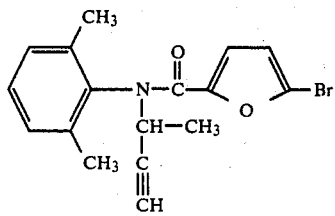

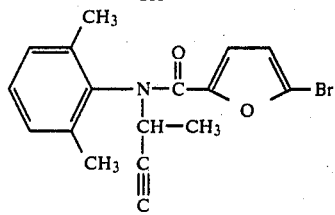

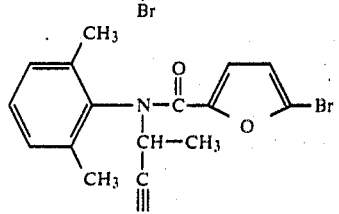

and

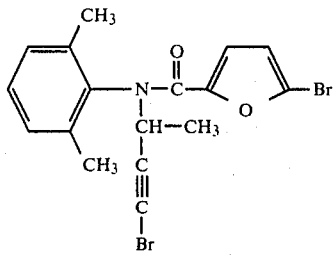

The invention further provides a process for combating the fungal diseases *Phytophthora infestans* (late blight on potatoes and tomatoes), and *Plasmopara viticola* (downy mildew on vines), which comprises treating plants or seeds, or their loci, with an alkynyl acylanilide derivative as defined in the preceding paragraphs.

The invention is illustrated by the specific compounds listed in Table I below. These correspond to the general formula:

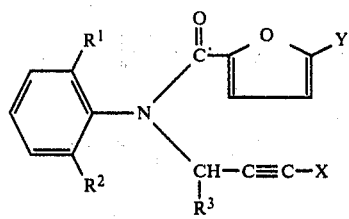

wherein $R^1$, $R^2$, $R^3$, X and Y are as indicated in the columns so headed.

TABLE I

| COMPOUND NO. | $R^1$ | $R^2$ | $R^3$ | X | Y | MELTING POINT °C. (BOILING POINT (BATH)/PRESSURE (mm Hg)) |
|---|---|---|---|---|---|---|
| 1 | CH₃ | CH₃ | CH₃ | H | Br | 90–91° C. |
| 2 | CH₃ | CH₃ | CH₃ | Br | Br | 74–76° C. |
| 3 | CH₃ | CH₃ | CH₃ | I | Br | 130–131° C. |
| 4 | CH₃ | CH₃ | CH₃ | Br | NO₂ | 92–93° C. |
| 5 | CH₃ | CH₃ | H | H | Br | |
| 6 | CH₃ | CH₃ | H | Br | Br | |
| 7 | CH₃ | CH₃ | CH₃ | H | OCH₃ | |
| 8 | CH₃ | CH₃ | CH₃ | Br | OCH₃ | |
| 9 | CH₃ | CH₃ | H | H | OCH₃ | |
| 10 | CH₃ | CH₃ | H | Br | OCH₃ | |
| 11 | CH₃ | CH₃ | CH₃ | H | Cl | |
| 12 | CH₃ | CH₃ | CH₃ | Br | Cl | |
| 13 | CH₃ | CH₃ | H | H | Cl | |
| 14 | CH₃ | CH₃ | H | Br | Cl | |

The alkynyl acylanilide derivatives of the invention can be made, for example, by the following, schematically represented process:

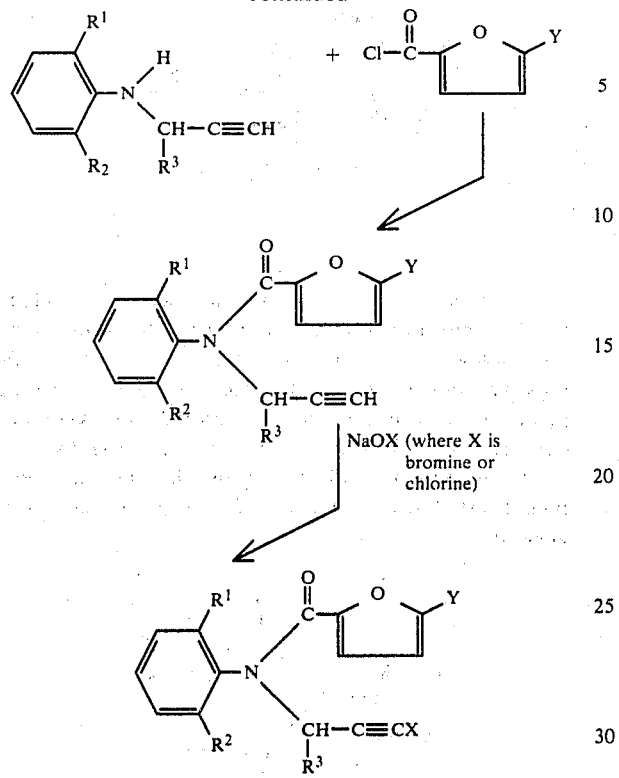

where $R^1$, $R^2$, $R^3$ and Y are as defined in the preceding paragraphs.

Thus there may be brought into reaction a substituted furan carboxylic acid halide of formula:

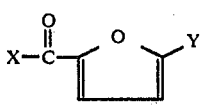

wherein X is halogen and Y is halogen, nitro or alkoxy, with a 2,6-disubstituted alkylidyne anilino derivative of formula:

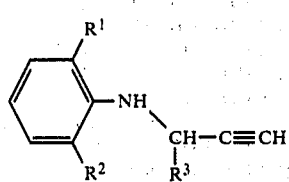

wherein $R^1$, $R^2$ and $R^3$ are as defined in any of claims 1, 2 and 3 and thereafter, if necessary, bringing the product into reaction with an alkali metal hypobromite or hypochlorite or iodine.

The starting alkylidyne anilino derivative may be prepared by bringing a 2,6-disubstituted aniline into reaction with a halo-alkylidyne.

The starting 2-substituted furan-2-carboxylic acid halide may be produced by bringing into reaction a 5-substituted furan and thionyl chloride.

The derivatives and compositions containing them are variously active against a wide range of fungal diseases, particularly, for example against:

(a) *Phytophthora infestans* (late blight) on potatoes and tomatoes
(b) Powdery mildews, for example:
 *Erysiphe graminis* on cereals
 *Sphaerotheca fuliginea* on cucurbits
 *Podosphaera leucotricha* on apples
 *Uncinula necator* on vines
 and other powdery mildews on other hosts
(c) Other fungal diseases, for example:
 *Botrytis cinerea* (grey mould) on tomatoes, strawberries, vines and other hosts
 *Venturia inaequalis* (scab) on apples
 *Plasmopara viticola* (downy mildew) on vines
 *Pythium ultimum* (damping off of peas)
(d) *Cercospora arachidicola* on peanuts and other Cercospora species.
(e) Some of the derivatives display activity against the bacterial disease *Xanthomonas oryzae* (bacterial leaf blight) on rice A particularly valuable feature of the activity of the acylanilide derivatives is their systemic effect, i.e. their ability to move in a plant to combat an infection or infestation remote from the site of initial application. Thus a derivative, or a composition containing it, may be applied to the soil surrounding the roots of a plant or to the seed or to other plant areas, e.g. leaves, and be taken up by the plant through its roots, or other areas, to combat fungi locally or elsewhere on the plants.

The acylanilide derivatives may be used as such for pesticidal, especially anti-fungal, purposes but are more conveniently formulated into compositions for such usage.

The invention also provides pesticidal, especially fungicidal, compositions comprising as active ingredient an acylanilide derivative as defined in any of the paragraphs above.

The acylanilide derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to soil surrounding the roots.

The term "treating" as used herein refers to all these modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion or emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The derivatives can be used in smoke generators and also as mixtures with fertilisers (e.g. nitrogen- or phosphorus-containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-ionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10-85%, generally 25-60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, for example other fungicides such as dithiocarbamates, dinocap, dichlofluanid and the like, as well as stabilising agent(s), for example epoxides (e.g. epichlorhydrin).

The invention is illustrated by the following Examples wherein the temperatures are in °C.

EXAMPLE 1

This Example illustrates the preparation of N-(2,6-Dimethylphenyl)-N-2(but-3-ynyl)-N-2(5-bromofurancarboxamide).

5-Bromofuran-2-carboxylic acid chloride (m.p. 58°-59° C., prepared from 5-bromo-2-furancarboxylic acid and thionyl chloride (1.7 g) was added to N-(2,6-dimethylphenyl)-N-2(but-3-ynyl) amine (1.4 g) in methylene chloride (30 ml) and pyridine (0.7 ml) to give the title compound (2.2 g), m.p. 90°-91° C. Found: C 58.4, H 4.5, N 4.0, Br 23.3%: Calculated for $C_{17}H_{16}NO_2Br$: C 58.9, H 4.6, N 4.0, Br 23.1%.

EXAMPLE 2

This Example illustrates the preparation of N-(2,6-Dimethylphenyl)-N-2(4-bromobut-3-ynyl)-N-2(5-bromofurancarboxamide).

N-(2,6-Dimethylphenyl)-N-2(but-3-ynyl)-N-2(5-bromofurancarboxamide) (6.9 g) in glyme (38 ml) was added to sodium hypobromite solution (prepared from 7.2 g sodium hydroxide in 15 ml. water and 2.3 ml bromine at 0°-10° C.) and the mixture stirred for 2 hours, poured into water, the oil product extracted into ether and solvent evaporated to give the title compound (9.1 g), m.p. 74°-76° C. Found: C 48.5, H 3.5, N 3.4%; Calculated for $C_{17}H_{15}NO_2Br_2$: C 48.0, H 3.5, N 3.3%.

EXAMPLE 3

This Example illustrates the preparation of N-(2,6-Dimethylphenyl)-N-2(iodobut-3-ynyl)-N-2(5-nitrofurancarboxamide).

To N-(2,6-Dimethylphenyl)-N-2(but-3-ynyl)-N-2(5-bromofurancarboxamide) (2.0 g) in methanol (25 ml) was added a methanolic solution of sodium hydroxide (7.5 ml 10% w/v) and methanol then added to dilute the solution to 175 ml. The solution was stirred and cooled to 10° C. and powdered iodine (1.5 g) added slowly, stirred 3 hours at room temperature, neutralised with hydrochloric acid and methanol evaporated to give title compound (2.2 g) m.p. 130°-131° C.

Found; C 43.8, H 3.3, N 3.0%; Calculated for $C_{17}H_{15}NO_2BrI$: C 43.2, H 3.2, N 3.0%.

EXAMPLE 4

This Example illustrates the preparation of N(2,6-Dimethylphenyl)-N-2(but-3-ynyl)-N-2(5-nirofurancarboxamide).

5-Nitrofuran-2-carboxylic acid chloride (prepared from 5-nitrofuran-2-carboxylic acid and thionyl chloride) in methylene chloride (25 ml) was added to N-(2,6-dimethylphenyl)-N-2(but-3-ynyl) amine (1.0 g) and pyridine (0.5 ml) in methylene chloride (20 ml) to give starting materials and the title compound (0.2 g) m.p. 92°-93° C.

Found: C 65.5, H 5.3, N 8.7%; Calculated for $C_{17}H_{16}N_2O_4$: C 65.4, H 5.1, N 8.9%.

EXAMPLE 5

An emulsifiable concentrate was made up by mixing the ingredients, and stirring the mixture until all the constitutents were dissolved.

Compound no. 1 of Table 1: 10%
Ethylene dichloride: 40%
Calcium dodecylbenzenesulphate: 5%
"Lubrol" L: 10%
Aromasol" H: 35%

EXAMPLE 6

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

Compound No. 2 of Table 1: 50%
"Dispersol" T: 25%
"Lubrol" APN 5: 1.5%
Sodium acetate: 23.5%

EXAMPLE 7

The ingredients were all ground together to produce a powder formulation readily dispersible in liquids.

Compound No. 3 of Table 1: 45%
"Dispersol" T: 5%
"Lissapol" NX: 0.5%
"Cellofas" B600: 2%
Sodium acetate: 47.5%

EXAMPLE 8

The active ingredient was dissolved in a solvent and the resultant liquid was sprayed on to the granules of China clay. The solvent was then allowed to evaporate to produce a granular composition.

Compound No. 4 of Table 1: 5%
China clay granules: 95%

EXAMPLE 9

A composition suitable for use as a seed dressing was prepared by mixing the three ingredients.

Compound No. 1 of Table 1: 50%
Mineral oil: 2%
China clay: 48%

EXAMPLE 10

A dusting powder was prepared by mixing the active ingredient with talc.

Compound No. 2 of Table 1: 5%
Talc: 95%

EXAMPLE 11

A Col formulation was prepared by ball-milling the constituents set out below and then forming an aqueous suspension of the ground mixture with water.

Compound No. 3 of Table 1: 40%
"Dispersol" T: 10%
"Lubrol" APN5: 1%
Water:

EXAMPLE 12

A dispersible powder formulation was made by mixing together the ingredients set out below and then grinding the mixture until all were thoroughly mixed.

Compound No. 4 of Table 1: 25%
"Aerosol" OT/B: 2%
"Dispersol" A.C.: 5%
China clay: 28%
Silica: 40%

EXAMPLE 13

This Example illustrates the preparation of a dispersible powder formulation. The ingredients were mixed and the mixture then ground in a comminution mill.

Compound No. 1 of Table 1: 25%
"Perminal" BX: 1%
"Dispersol" T: 5%
Polyvinylpyrrolidone: 10%
Silica: 25%
China clay: 34%

EXAMPLE 14

The ingredients set out below were formulated into a dispersible powder by mixing the grinding the ingredients.

Compound No. 2 of Table 1: 25%
"Aerosol" OT/B: 2%
"Dispersol" A: 5%
China clay: 68%

In Examples 5 to 14 the proportions of the ingredients given are by weight.

There now follows an explanation of the compositions or substances represented by the various Trade Marks and Trade Names mentioned above.

LUBROL L: a condensate of nonyl phenol (1 mole) with ethylene oxide (13 moles)

AROMASOL H: a solvent mixture of alkylbenzenes

DISPERSOL T AND AC: a mixture of sodium sulphate and a condensate of formaldehyde with sodium naphthalene sulphonate.

LUBROL APN 5: a condensate of nonyl phenol (1 mole) with naphthalene oxide (5.5 moles).

CELLOFAS B600: a sodium carboxymethyl cellulose thickener.

LISSAPOL NX: a condensate of nonyl phenol (1 mole) with ethylene oxide (8 moles).

AERSOL OT/B: dioctyl sodium sulpho succinate.

PERMINAL BX: a sodium alkyl naphthalene sulphonate.

EXAMPLE 15

Compounds of Table 1 were tested against a variety of foliar fungal diseases of plants. The technique employed was as follows.

The plants were grown in John Innes Potting Compost (No. 1, or No. 2, as appropriate) in 4 cm diameter minipots. A layer of fine sand was placed at the bottom of the pot to facilitate uptake of test compound by the roots.

The test compounds were formulated either by beadmilling with aqueous Dispersol T or as a solution in acetone/ethanol which was diluted to the required concentration immediately before use. For the tests conducted, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). An exception is the test on *Plasmopara viticola* in which the chemical is applied to the foliage only.

For the tests, the test compound was applied to the soil (roots) and to the foliage (by spraying) one or two days before the plant was innoculated with the diseases. After innoculation, the plants were put into an appropriate environment to allow infection to take place and then incubated until the disease was ready for assessment. The period between inoculation and assessment varied from 3 to 6 days according to the disease and environment, as shown in Table II below.

TABLE II

| DISEASE AND PLANT | INTERVAL USUAL TIME (DAYS)* |
|---|---|
| (1) *Phytophthora infestans* (tomato) | 3 |
| (2) *Plasmopara viticola* (vine) | 6 |

*N.B. These intervals are not rigid and will vary with the individual tests. Assessment is normally done at the point of optimum disease development commensurate with a practical timetable.

The disease control was recorded by the following gradings:
4 = No disease
3 = 0-5%
2 = 6-25%
1 = 26-60%
0 = 60%

The results are shown in Table III.

TABLE III

| COMPOUND NO. | PHYTOPHTHORA INFESTANS (tomato) | PLASMOPARA VITICOLA (vine) |
|---|---|---|
| 1 | 4 | 4 |
| 2 | 3 | 4 |
| 3 | 3 | 4 |
| 4 | 4 | 3 |

We claim:

1. Alkynyl acylanilide derivatives having the formula:

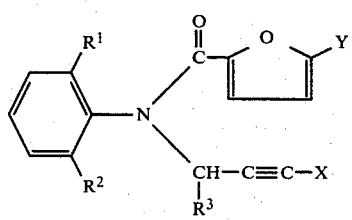

wherein $R^1$ and $R^2$ are lower alkyl groups containing from 1 to 4 carbon atoms; $R^3$ is hydrogen or a lower alkyl group containing from 1 to 4 carbon atoms; X is hydrogen or halogen; and Y is halogen, nitro or an alkoxy group containing from 1 to 4 carbon atoms.

2. An alkynyl acylanilide derivative as claimed in claim 1 wherein $R^1$, $R^2$ and $R^3$ are methyl radicals, X is hydrogen, bromine, iodine or chlorine, and Y is chlorine, bromine, nitro or methoxy.

3. Alkynyl acylanilide derivatives having the formulae

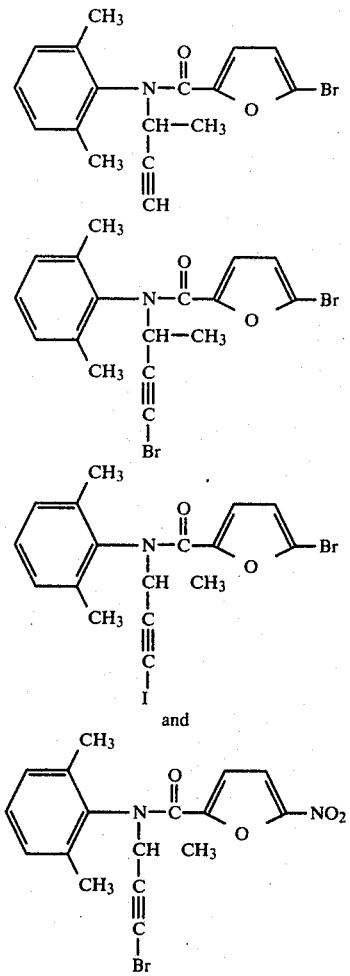

and

4. A process for combating pests which comprises applying to plants or seeds, or to their loci, a pesticidally effective amount of an acylanilide derivative as defined in any of claims 1 to 3.

5. A process for combating the fungal diseases *Phytophthora infestans* (late blight on potatoes and tomatoes), and *Plasmopara viticola* (downy mildew on vines), which comprises treating the plants or seeds, or their loci, with a fungicidally effective amount of an acylanilide derivative as defined in any of claims 1 to 3.

6. A pesticidal composition comprising, as an active ingredient, a pesticidally effective amount of an alkynyl acylanilide derivative as defined in any of claims 1, to 3.